United States Patent
Hanbury (10) Patent No.: US 11,298,502 B2
(45) Date of Patent: Apr. 12, 2022

(54) NON-PHARMACEUTICAL METHODS OF MITIGATING ADDICTION WITHDRAWAL SYMPTOMS

(71) Applicant: SANA HEALTH, INC., Lafayette, CO (US)

(72) Inventor: Richard Hanbury, Lafayette, CO (US)

(73) Assignee: SANA HEALTH, INC., Lafayette, CO (US)

( * ) Notice: Subject to any disclaimer, the term of this patent is extended or adjusted under 35 U.S.C. 154(b) by 346 days.

(21) Appl. No.: 16/459,318

(22) Filed: Jul. 1, 2019

(65) Prior Publication Data

US 2019/0321585 A1    Oct. 24, 2019

Related U.S. Application Data

(63) Continuation-in-part of application No. 16/422,592, filed on May 24, 2019, now Pat. No. 11,141,559, and
(Continued)

(51) Int. Cl.
*A61M 21/02* (2006.01)
*A61M 21/00* (2006.01)

(52) U.S. Cl.
CPC ....... *A61M 21/02* (2013.01); *A61M 2021/005* (2013.01); *A61M 2021/0022* (2013.01); *A61M 2021/0027* (2013.01); *A61M 2205/3569* (2013.01); *A61M 2205/3592* (2013.01); *A61M 2205/505* (2013.01); *A61M 2209/088* (2013.01)

(58) Field of Classification Search
CPC .............................................. A61M 21/00–02
See application file for complete search history.

(56) References Cited

U.S. PATENT DOCUMENTS

| 4,172,406 A | 10/1979 | Martinez |
| 4,315,502 A | 2/1982 | Gorges |

(Continued)

FOREIGN PATENT DOCUMENTS

| CN | 205814527 U | 12/2016 |
| CN | 104546285 B | 3/2017 |

(Continued)

OTHER PUBLICATIONS

International Searching Authority, Search Report and Written Opinion in PCT/US2020/019091, dated May 6, 2020; 13 pages.
(Continued)

*Primary Examiner* — Thaddeus B Cox
(74) *Attorney, Agent, or Firm* — Dickinson Wright, PLLC; Stephen A. Mason (57) ABSTRACT

Non-pharmaceuticals method of treating the effects of addiction withdrawal are described. The method includes providing a person with stimuli include visual and/or auditory stimuli which are pulsed at the rate of various types of brain waves. The use of the method lessens various withdrawal symptoms, such as anxiety, sleepiness, sweating, tearing of the eyes, running of the nose, goosebumps, shaking, hot flushes, cold flushes, bones aching, muscles aching, restlessness, nausea, vomiting, muscle twitching, stomach cramps, pain, the need to use an opioid, the desire to use an opioid, sleep disturbances. and the use of rescue medications.

37 Claims, 7 Drawing Sheets

Related U.S. Application Data a continuation-in-part of application No. 15/910,252, filed on Mar. 2, 2018, now Pat. No. 10,799,667, which is a continuation of application No. 15/360,808, filed on Nov. 23, 2016, now Pat. No. 10,328,236.

(60) Provisional application No. 62/808,676, filed on Feb. 21, 2019, provisional application No. 62/466,281, filed on Mar. 2, 2017, provisional application No. 62/258,965, filed on Nov. 23, 2015.

(56) References Cited

U.S. PATENT DOCUMENTS

| | | | |
|---|---|---|---|
| 4,892,106 A | 1/1990 | Gleeson | |
| 4,966,164 A * | 10/1990 | Colsen | A61H 39/002 607/72 |
| 5,343,261 A | 8/1994 | Wilson | |
| 5,783,909 A | 7/1998 | Hochstein | |
| 6,123,661 A | 9/2000 | Fukushima et al. | |
| 6,409,655 B1 | 6/2002 | Wilson et al. | |
| 8,562,659 B2 | 10/2013 | Wells et al. | |
| 8,838,247 B2 | 9/2014 | Hagedorn et al. | |
| 8,852,073 B2 | 10/2014 | Genereux et al. | |
| 8,932,199 B2 | 1/2015 | Berka et al. | |
| D775,260 S | 12/2016 | Gordon et al. | |
| 9,649,469 B2 * | 5/2017 | Hyde | G16H 20/10 |
| D805,515 S | 12/2017 | Bowes et al. | |
| D827,701 S | 9/2018 | Nguyen et al. | |
| 10,328,236 B2 | 6/2019 | Hanbury | |
| 10,383,769 B1 | 8/2019 | Miller | |
| 10,449,326 B2 | 10/2019 | Genereux et al. | |
| 2002/0198577 A1 | 12/2002 | Jaillet | |
| 2006/0106276 A1 | 5/2006 | Shealy et al. | |
| 2006/0252979 A1 | 11/2006 | Vesely et al. | |
| 2008/0269629 A1 | 10/2008 | Reiner | |
| 2009/0156886 A1 | 6/2009 | Burgio et al. | |
| 2010/0056854 A1 | 3/2010 | Chang | |
| 2010/0161010 A1 | 6/2010 | Thomas | |
| 2010/0323335 A1 | 12/2010 | Lee | |
| 2011/0075853 A1 | 3/2011 | Anderson | |
| 2011/0213664 A1 | 9/2011 | Osterhout et al. | |
| 2011/0257712 A1 | 10/2011 | Wells et al. | |
| 2012/0095534 A1 | 4/2012 | Schlangen et al. | |
| 2012/0211013 A1 | 8/2012 | Otis | |
| 2013/0035734 A1 | 2/2013 | Soler Fernandez et al. | |
| 2013/0225915 A1 | 8/2013 | Redfield et al. | |
| 2013/0267759 A1 | 10/2013 | Jin | |
| 2013/0303837 A1 | 11/2013 | Berka et al. | |
| 2014/0336473 A1 | 11/2014 | Greco | |
| 2015/0231395 A1 | 8/2015 | Saab | |
| 2015/0268673 A1 | 9/2015 | Farzbod et al. | |
| 2016/0228771 A1 * | 8/2016 | Watson | A61B 5/4023 |
| 2017/0143935 A1 | 5/2017 | Hanbury | |
| 2017/0189639 A1 | 7/2017 | Mastrianni | |
| 2017/0252532 A1 | 9/2017 | Holsti et al. | |
| 2017/0312476 A1 | 11/2017 | Woo | |
| 2018/0184969 A1 | 7/2018 | Zhao et al. | |
| 2018/0250494 A1 | 9/2018 | Hanbury | |
| 2019/0030279 A1 | 1/2019 | Nowlin | |
| 2019/0192077 A1 | 6/2019 | Kaiser et al. | |
| 2019/0262576 A1 | 8/2019 | Mastrianni | |
| 2019/0388020 A1 | 12/2019 | Stauch et al. | |
| 2020/0139112 A1 | 5/2020 | Aharonovitch | |
| 2020/0268341 A1 | 8/2020 | Stroman | |
| 2020/0368491 A1 | 11/2020 | Poltorak | |
| 2021/0008332 A1 | 1/2021 | Jin et al. | |

FOREIGN PATENT DOCUMENTS

| | | |
|---|---|---|
| WO | 2001064005 A2 | 9/2001 |
| WO | 2012117343 A1 | 9/2012 |
| WO | 2015028480 A1 | 3/2015 |
| WO | 2016140408 A1 | 9/2016 |
| WO | 2019060598 A1 | 3/2019 |
| WO | 2020219350 A1 | 10/2020 |

OTHER PUBLICATIONS

Chinnakkaruppan Adaikkan, et al., "Gamma Entrainment Binds Higher-Order Brain Regions and Offers Neuroprotection", Neuron, https://linkinghub.elsevier.com/retrieve/pii/S0896627319303460, May 7, 2019 (May 7, 2019), 18 Pages.

Liviu Aron, et al., "Neural synchronization in Alzheimer's disease", Nature, Journal, vol. 540, Dec. 7, 2016 (Dec. 7, 2016), pp. 207-208.

Pam Belluck, "Could simply listening to this sound help cure Alzheimer's disease? MIT researchers are investigating", Boston Globe, https://www.bostonglobe.com/news/science/2019/03/14/could-simply-listening-this-sound-help-cure-alzheimer-disease-mit-researchers-are-investigating/2npZrAp8g9kLSfURbTxaVO/story.html, Mar. 14, 2019 (Mar. 14, 2019), 4 Pages.

Pam Belluck, "A Possible Alzheimer's Treatment With Clicks and Flashes? It Worked on Mice", New York Times, https://www.nytimes.com/2019/03/14/health/alzheimers-memory.html, Mar. 14, 2019 (Mar. 14, 2019), 5 Pages.

Angus Chen, "An Hour of Light and Sound a Day Might Keep Alzheimer's at Bay", Scientific American, https://www.scientificamerican.com/article/an-hour-of-light-and-sound-a-day-might-keep-alzheimers-at-bay/, Mar. 14, 2019 (Mar. 14, 2019), 5 Pages.

Aimee Corso, "Cognito Therapeutics Launched with Exclusive License to Promising Alzheimer's Research from The Massachusetts Institute of Technology", Business Wire, Boston and San Francisco, https://www.businesswire.com/news/home/20161207006042/en/Cognito-Therapeutics-Launched-Exclusive-License-Promising-Alzheimer%E2%80%99s, Dec. 7, 2016 (Dec. 7, 2016), 3 Pages.

Hannah Devlin, "Strobe lighting provides a flicker of hope in the fight against Alzheimer's", The Guardian, https://www.theguardian.com/science/2016/dec/07/strobe-lighting-provides-a-flicker-of-hope-in-the-fight-against-alzheimers, Dec. 7, 2016 (Dec. 7, 2016), 3 Pages.

Jamie Ducharme, "The End of Alzheimer's?", Boston, Magazine, https://www.bostonmagazine.com/health/2017/11/27/li-huei-tsai-alzheimers-treatment/, Nov. 27, 2017 (Nov. 27, 2017), 4 Pages.

Damian Garde, "'Beyond amyloid': A look at what's next in Alzheimer's research", STAT, https://www.statnews.com/2017/08/18/beyond-amyloid-alzheimers-research/, Aug. 18, 2017 (Aug. 18, 2017), 5 Pages.

Melissa Healy, "Flickering lights may illuminate a path to Alzheimer's treatment", Los Angeles Times, Dec. 7, 2016 (Dec. 7, 2016), 3 Pages.

Nathan Hurst, "Could Flickering Lights Help Treat Alzheimer's?", Smithsonian, https://www.smithsonianmag.com/innovation/could-flickering-lights-help-treat-alzheimers-180961762/, Jan. 11, 2017 (Jan. 11, 2017), 2 Pages.

Hannah F. Iaccarino, et al., "Gamma frequency entrainment attenuates amyloid load and modifies microglia", Nature, Journal, vol. 540, Dec. 7, 2016 (Dec. 7, 2016), pp. 230-235.

Anthony J. Martorell, et al., "Multi-sensory Gamma Stimulation Ameliorates Alzheimer's-Associated Pathology and Improves Cognition", Cell, https://www.cell.com/cell/fulltext/S0092-8674(19)30163-1, Mar. 14, 2019 (Mar. 14, 2019), 16 Pages.

Helen Thomson, "How flashing lights and pink noise might banish Alzheimer's, improve memory and more", Nature, https://www.nature.com/articles/d41586-018-02391-6, Feb. 28, 2018 (Feb. 28, 2018), 10 Pages.

Meg Tirrell, "Could flashing light treat Alzheimer's? Fresh approaches to treating the disease", CNBC, https://www.cnbc.com/2017/03/29/could-flashing-light-treat-alzheimers-fresh-approaches-to-treating-the-disease.html, Mar. 29, 2017 (Mar. 29, 2017), 6 Pages.

Anne Trafton, "Ed Boyden receives 2018 Canada Gairdner International Award", McGovern Institute, https://mcgovern.mit.edu/2018/03/27/ed-boyden-receives-2018-canada-gairdner-international-award/, Mar. 27, 2018 (Mar. 27, 2018), 3 Pages.

Molly Webster, et al., "Bringing Gamma Back", WNYC Studios, https://www.wnycstudios.org/story/bringing-gamma-back, Dec. 8, 2016 (Dec. 8, 2016), 3 Pages.

Robert Weisman, "MIT team uses LEDs to attack Alzheimer's", Boston Globe, https://www.bostonglobe.com/business/2016/12/07/

(56) References Cited

OTHER PUBLICATIONS led-technology-from-mit-used-startup-working-alzheimer-treatment/Kbdjp9WvfoPLfC1bNhvGOI/story.html, Dec. 7, 2016 (Dec. 7, 2016), 4 Pages.

Nicole Wetsman, "Flickering light seems to help mice with Alzheimer's-like symptoms", Popular Science, https://www.popsci.com/flickering-light-genes-alzheimers, May 7, 2019 (May 7, 2019), 2 Pages.

Ed Yong, "Beating Alzheimer's With Brain Waves", The Atlantic, https://www.theatlantic.com/science/archive/2016/12/beating-alzheimers-with-brain-waves/509846/, Dec. 7, 2016 (Dec. 7, 2016), 8 Pages.

North Shore Technology Council, "First Friday Biosciences: Nov. 3 in Woburn", https://www.nstc.org/previous-events/first-friday-biosciences-nov-3-in-woburn/, Nov. 3, 2017 (Nov. 3, 2017), 8 Pages.

The Picower Institute, "Tsai earns Hans Wigzell Research Foundation Science Prize", https://picower.mit.edu/news/tsai-earns-hans-wigzell-research-foundation-science-prize, Jan. 23, 2019 (Jan. 23, 2019), 3 Pages.

PCT Search Report and Written Opinion, dated May 7, 2018 in International Application PCT/US2018020547, filed Mar. 1, 2018, 10 pages.

PCT Search Report and Written Opinion, dated Feb. 3, 2017 in International Application PCT/US2016063651, filed Nov. 23, 2016, 13 pages.

Intellectual Property India, Examination Report for Application No. 201837022885, dated May 6, 2021; 7 pages.

European Patent Office, Extended European Search Report dated Nov. 27, 2020 for European Patent Application No. 18761087.8, 9 pages.

Illumy by Sound Oasis; https://www.soundoasis.com/products/light-therapy/illumy-the-smart-sleep-mask/; Product description downloaded Aug. 2, 2021; 6 pages Copyright 2000-2021 AvivaHealth.com.

Remee Lucid Dreaming Mask; http://sleepwithremee.com/; Product description downloaded Aug. 3, 2021; 10 pages; Copyright 2018 Bitbanger LLC.

Lumos Smart Sleep Mask; https://lumos.tech/lumos-smart-sleep-mask/; Product description downloaded Aug. 3, 2021; 3 pages.

Dreamlight Zen; https://dreamlight.tech/products/dreamlight-zen; product description downloaded Aug. 3, 2021; 16 pages; Copyright 2021 Dreamlight.

European Patent Office, Supplementary European Search Report dated Jun. 5, 2019 for European Patent Application No. 16869299.4, eight pages.

The International Searching Authority, Notification of Transmittal of the International Search Report and the Written Opinion of the International Searching Authority dated Aug. 2, 2019 in International Application No. PCT/US19/033322, 19 pages.

International Searching Authority, Search Report and Written Opinion in PCT/US20/41423, dated Oct. 9, 2020; 9 pages.

International Search Report and Written Opinion in PCT/US2021/032260, dated Aug. 31, 2021; 9 pages.

Szafir, et al., Pay Attention Designing Adaptive Agents that Monitor and Improve User Engagement, Conference on Human Factors in Computing Systems, May 5, 2012, 10 Pages.

\* cited by examiner

| Segments A1-A4 for 120s | Auditory Left | Auditory Right | Light Left | Light Right |
|---|---|---|---|---|
| Segment A1 (Light and Auditory both sides pulse together) Repeat 116 times, followed by 0.5 sec gap | On 0.1277 sec | On 0.1277 sec | On 0.1277 sec | On 0.1277 sec |
| | Off 0.1277 sec | Off 0.1277 sec | Off 0.1277 sec | Off 0.1277 sec |
| Segment A2 (light and auditory on left side, alternating light and auditory on right). Repeat 116 times, followed by 0.5 sec gap | On 0.1277 sec | Off 0.1277 sec | On 0.1277 sec | Off 0.1277 sec |
| | Off 0.1277 sec | On 0.1277 sec | Off 0.1277 sec | On 0.1277 sec |
| Segment A3 (both lights together, alternating with both auditory signals together) Repeat 115 times, followed by 0.5 sec gap | On 0.1277 sec | On 0.1277 sec | Off 0.1277 sec | Off 0.1277 sec |
| | Off 0.1277 sec | Off 0.1277 sec | On 0.1277 sec | On 0.1277 sec |
| Segment A4 (auditory left and light right together, alternating auditory right and light left together) Repeat 115 times, followed by 0.5 sec gap | On 0.1277 sec | Off 0.1277 sec | Off 0.1277 sec | On 0.1277 sec |
| | Off 0.1277 sec | On 0.1277 sec | On 0.1277 sec | Off 0.1277 sec |

| Segments B1-B4 for 120s | Auditory Left | Auditory Right | Light Left | Light Right |
|---|---|---|---|---|
| Segment B1 (Light and Auditory both sides pulse together) Repeat 45 times, followed by 0.5 sec gap | On 0.3333 sec | On 0.3333 sec | On 0.3333 sec | On 0.3333 sec |
| | Off 0.3333 sec | Off 0.3333 sec | Off 0.3333 sec | Off 0.3333 sec |
| Segment B2 (light and auditory on left side, alternating light and auditory on right) Repeat 44 times, followed by 0.5 sec gap | On 0.3333 sec | Off 0.3333 sec | On 0.3333 sec | Off 0.3333 sec |
| | Off 0.3333 sec | On 0.3333 sec | Off 0.3333 sec | On 0.3333 sec |
| Segment B3 (both lights together, alternating with both auditory signals together) Repeat 44 times, followed by 0.5 sec gap | On 0.3333 sec | On 0.3333 sec | Off 0.3333 sec | Off 0.3333 sec |
| | Off 0.3333 sec | Off 0.3333 sec | On 0.3333 sec | On 0.3333 sec |
| Segment B4 (auditory left and light right together, alternating auditory right and light left together) Repeat 44 times, followed by 0.5 sec gap | On 0.3333 sec | Off 0.3333 sec | Off 0.3333 sec | On 0.3333 sec |
| | Off 0.3333 sec | On 0.3333 sec | On 0.3333 sec | Off 0.3333 sec |

FIG. 6

| Repeat the following Segments C1-C4 6 times for a total of 12 minutes | Auditory Left | Auditory Right | Light Left | Light Right |
|---|---|---|---|---|
| Segment C1 (Light and Auditory both sides pulse together) Repeat 15 times, followed by 1 sec gap | On 1 sec | On 1 sec | On 1 sec | On 1 sec |
| | Off 1 sec | Off 1 sec | Off 1 sec | Off 1 sec |
| Segment C2 (light and auditory on left side, alternating light and auditory on Right) Repeat 15 times, followed by 1 sec gap | On 1 sec | Off 1 sec | On 1 sec | Off 1 sec |
| | Off 1 sec | On 1 sec | Off 1 sec | On 1 sec |
| Segment C3 (both lights together, alternating with both auditory signals together) Repeat 14 times, followed by 1 sec gap | On 1 sec | On 1 sec | Off 1 sec | Off 1 sec |
| | Off 1 sec | Off 1 sec | On 1 sec | On 1 sec |
| Segment C4 (auditory left and light right together, alternating auditory right and light left together) Repeat 14 times, followed by 1 sec gap | On 1 sec | Off 1 sec | Off 1 sec | On 1 sec |
| | Off 1 sec | On 1 sec | On 1 sec | Off 1 sec |

FIG. 7

NON-PHARMACEUTICAL METHODS OF MITIGATING ADDICTION WITHDRAWAL SYMPTOMS

CROSS-REFERENCE TO RELATED APPLICATIONS

This application claims the benefit of U.S. Provisional Application No. 62/808,676, filed Feb. 21, 2019, and is a Continuation-In-Part of U.S. patent application Ser. No. 15/910,252, filed on Mar. 2, 2018, now U.S. Pat. No. 10,799,667, which claims the benefit of U.S. Provisional Application No. 62/466,281 filed on Mar. 2, 2017, and is a Continuation-In-Part of U.S. patent application Ser. No. 16/422,592 filed on May 24, 2019, now U.S. Pat. No. 11,141,559, which is a Continuation of U.S. patent application Ser. No. 15/360,808 filed on Nov. 23, 2016, now U.S. Pat. No. 10,328,236, which claims the benefit of U.S. Provisional Application No. 62/258,965 filed on Nov. 23, 2015.

BACKGROUND OF THE INVENTION

Field of the Invention

The present invention generally relates to assisting those attempting to eliminate addictions, and more particularly to a non-pharmaceutical method of mitigating addictive substance withdrawal symptoms.

Discussion of the Background

The National Survey on Drug Use and Health (NSDUH) estimates that 19.7 million American adults battled a substance use disorder in 2017. Of these Americans, almost 74% of adults struggled with an alcohol use disorder and about 38% of adults battled an illicit drug use disorder. Drug abuse and addiction cost American society more than $740 billion annually in lost workplace productivity, healthcare expenses, and crime-related costs. Substance use which may result in addiction includes a variety of legal and illegal drugs, and alcohol and nicotine.

Addictive substances can cause a physical dependence that is usually difficult to overcome and results in a tolerance that requires higher doses over time. It may be extremely difficult for a person to stop taking a substance to which there are addictive. In particular, the human body responds to an abrupt discontinuation or decrease in intake of addictive substances with withdrawal symptoms. Withdrawal symptoms from opiates include anxiety, sweating, vomiting, and diarrhea. Alcohol withdrawal symptoms include irritability, fatigue, shaking, sweating, and nausea. Withdrawal from nicotine can cause irritability, fatigue, insomnia, headache, and difficulty concentrating. Many prescription and legal nonprescription substances can also cause withdrawal symptoms when individuals stop consuming them, even if they were taken as directed by a physician.

In addition to withdrawal symptoms, misusing opioids can result in death. Opioids are a class of drugs that include the heroin, synthetic opioids such as fentanyl, and pain relievers available legally by prescription, such as oxycodone (OXYCONTIN'), hydrocodone (VICODIN®), codeine, and morphine. The number of opioid overdose deaths has increased in recent decades and has reached epidemic proportions.

Current methods of treating opioid withdrawal symptoms includes providing medications such as methadone, buprenorphine, or naltrexone to a patient. Once treatment is initiated, both a buprenorphine/naloxone combination and an extended release naltrexone formulation are similarly effective in treating opioid addiction. These medications help many people recover from opioid addiction.

There is a need for tools and methods of addressing addiction. There is also a need for tools and methods of lessening the effects of addiction withdrawal symptoms that do not rely on pharmaceuticals.

BRIEF SUMMARY OF THE INVENTION

The present invention overcomes the disadvantages of the prior art by providing a non-pharmaceutical method of treating effects of addiction withdrawal.

It is one aspect of certain embodiments to provide a method of treating two or more symptoms in a person. The method includes administering a therapeutically effective amount of a sensory stimulus to the person, where the sensory stimulus includes one or more of a visual stimuli and an auditory stimuli. In one embodiment, the symptoms include anxiety, pain, sleepiness, sweating, tearing of the eyes, running of the nose, goosebumps, shaking, hot flushes, cold flushes, aching bones, aching muscles, restlessness, nausea, vomiting, muscle twitching, stomach cramps, pain, the need to use an opioid, the desire to use an opioid, and sleep disturbances.

It is another aspect of certain embodiments to treat symptoms for a person undergoing addiction withdrawal. In one aspect, the symptoms result opioid addiction. In another aspect, the symptoms result from nicotine addiction.

It is yet another aspect of certain embodiments to provide a method treating two or more symptoms, where the method includes providing a headset to be worn by the person and administering, with the headset, the therapeutically effective amount of a sensory stimulus to the person.

In certain embodiments sensory stimulus is provided to a person using devices and methods described in U.S. patent application Ser. No. 15/360,808 (the '808 patent application) and in U.S. patent application Ser. No. 15/910,252 (the '252 patent application). The '808 and '252 patent applications are co-owned with the present patent application and are both herein included by way of incorporation in their entirety.

These features together with the various ancillary provisions and features which will become apparent to those skilled in the art from the following detailed description are attained by the method of the present invention, preferred embodiments thereof being shown with reference to the accompanying drawings, by way of example only, wherein:

BRIEF DESCRIPTION OF THE SEVERAL VIEWS OF THE DRAWING

FIGS. 2A, 2B, and 2C are a bottom right perspective view, a rear view, and a left view, respectively.

Reference symbols are used in the Figures to indicate certain components, aspects or features shown therein, with

DETAILED DESCRIPTION OF THE INVENTION

Various embodiments described herein are directed to non-pharmaceutical methods of managing pain. The methods include administering a therapeutically effective amount of a sensory stimulus to the person, resulting in a reduction of the person's perception of pain, and/or an improvement in the person's tolerance for pain.

The sensory stimulus provided to the person as described herein is provided over a period of time and may, in certain embodiments, comprise two or more simultaneous stimuli, such as a visual stimuli and an auditory stimuli. In addition, each sensory stimuli may include a temporal sequence of sensory stimuli patterns, such as a sequence of stimuli having different frequencies, and/or a stimuli that alternates between sensory organs, as by alternating between the eyes or ears or the person. In various embodiments, the stimulus may include, but is not limited to, one or more of: a visual stimuli to one or both eyes of the person; an auditory stimuli to one or both ears of the person; and/or a tactile stimuli to the skin of the person.

Figure 1:
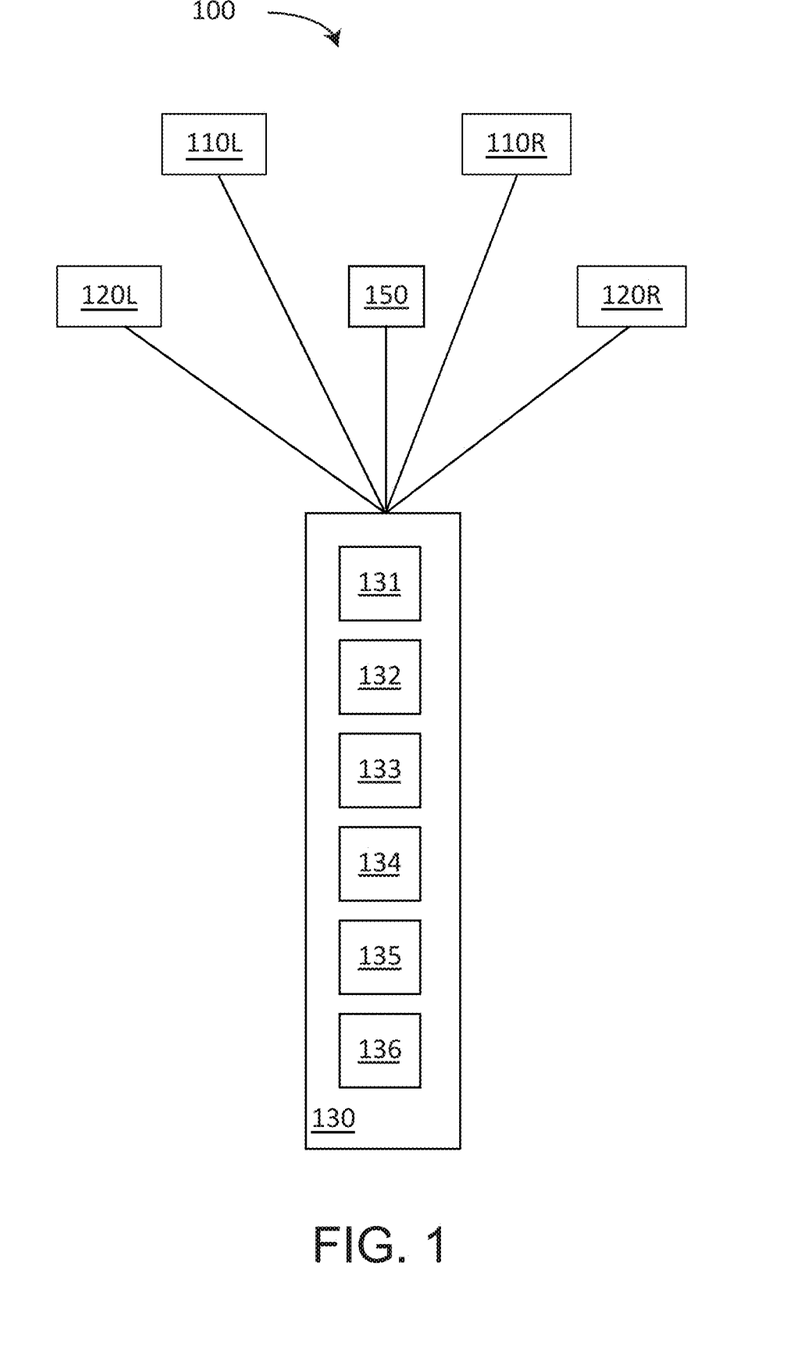
FIG. 1 is a schematic diagram of a system that may be used to provide a therapeutic sensory stimulus to a person.

FIG. 1 is a schematic diagram of a system 100 that may be used to provide a therapeutic sensory stimulus to a person. System 100 provides one or more stimuli outputs that a person wearing the system may experience as an auditory stimuli, a visual stimuli, and/or tactile stimuli. In one embodiment, system 100 comprises a left light source 110L, a right light source 110R, a left vibration source 120L, a right vibration source 120R, and a controller 130 for independently controlling and coordinating the action of the light and vibration sources. Thus, for example, system 100 may be positioned on the head of a user with left light source 110L positioned over the left eye to provide a left visual stimulus, right light source 110R positioned over the right eye to provide a right visual stimulus, left vibration source 120L positioned to provide left ear auditory stimuli, and right vibration source 120R positioned to provide right ear auditory stimuli.

In one embodiment, left and right light sources 110L, 110R may each comprise light-emitting diodes, an incandescent light source having a wavelength filter, a fluorescent light source, a backlit LCD panel, or other light source configured to provide to the user light at a desired, predetermined wavelength or wavelength range.

In one embodiment, left and right vibration sources 120L, 120R may each comprise earbuds, miniature speakers, or other vibration sources that can provide auditory stimuli to a user. In certain other embodiments, left and right vibration sources 120L, 120R may comprise bone conduction transducers in the audible frequency range to provide vibrations to the user's skull bone that is sensed as auditory by the user's ear. Optionally, one or more of left and right vibration sources 120L, 120R may also produce vibrations that are sensed as tactile stimuli. Thus, for example, controller 130 may provide first signals to bone conduction transducers that vibrate or oscillate at a first frequency that can be interpreted by the user as auditory stimuli and may provide second signals at a second, lower frequency that can be interpreted as a tactile sensation by the user. In other words, bone conduction transducers may be adapted to provide both auditory and tactile stimulus to the user.

In certain embodiments, left and right vibration sources 120L, 120R provide output at specific one or more frequencies or a range of frequencies. In one embodiment, left and right vibration sources 120L, 120R are separately controlled to provide output at certain times and to not provide output at other times. Thus, for example, a vibration source may be programmed to provide an output as an amplitude modulated audio frequency, which may be, for example and without limitation, 141 Hz, 174 Hz, 232 Hz or 256 Hz. Thus, in this example, the vibration source is the product of an audio frequency and a square wave.

In an alternative embodiment, left and right vibration sources 120L, 120R provide signals of slightly different frequencies to the left and right ear. This results in a binaural beats effect, wherein the person perceives a sound at a frequency that is the difference between the frequency in the right ear and the frequency in the left ear. Thus, for example, when a person is provided with a 200 Hz audio frequency to the left ear and a 210 Hz audio frequency to the right ear, the person will perceive 200 Hz in the left ear, 210 Hz in the right ear, and 210 Hz–200 Hz=10 Hz which appear as being provided to both ears. One skilled in the art may use this effect to provide sound at brain wave frequencies separately from, or in combination with, the other methods described herein.

System 100 also includes a sensor assembly 150 that obtains one or more measurements from the user. Thus, for example and without limitation, sensor 150 may include, or is in communication with, a sensor that measures some property or characteristic of the user, including but not limited to, heart rate, heart rate variability, body temperature, or blood pressure, and includes electronics that provide a signal indicative of the measurement to controller 130. In other embodiments, the sensors are connected to sensor assembly 150 by wired or wireless connectors. Thus, in various embodiments, the sensors may include one or more: electrodes for sensing electrical activity in the brain, as in a 2 or 4 lead EEG, a temperature sensor, and/or a heartbeat sensor, or one or more EMG sensors positioned, for example and without limitation, to measure eye movement to ascertain when REM sleep is reached, and/or to measure muscle tone to aid in determining states of relaxation. In certain embodiments, controller 130 utilizes the signal from sensor assembly 150 to modify the intensity and/or timing of the light and vibration sources.

In one embodiment controller 130 includes: an output 131 to provide signals to actuate light sources 110L and 110R, vibration sources 120L and 120R, and any other components that provide sensory input to the user; an input 132 to accept signals from sensor assembly 150; a non-transitory memory 133 for storing programming and data for system 100; a processor 134; and a communications module 135. Memory 133 includes instructions that are accessible to processor 134 for operating the components that provide sensory input to the user, including but not limited to light sources 110L and 110R, vibration sources 120L and 120R, including accepting input provided to input 132 and modifying signals provided to components that provide sensory input to the user, including but not limited to light sources 110L and 110R, vibration sources 120L and 120R. Communications module 135 provides for the transfer of information to or from controller 130 by wired or wireless means.

In an alternative embodiment, system 100 may also provide tactile stimulus to a user by including a left tactile stimulus source and a right tactile stimulus source (not shown), each of which may be individually controlled and coordinated with the controller 130 to provide tactile stimuli to a user of therapeutic system 100.

Figure 2A:
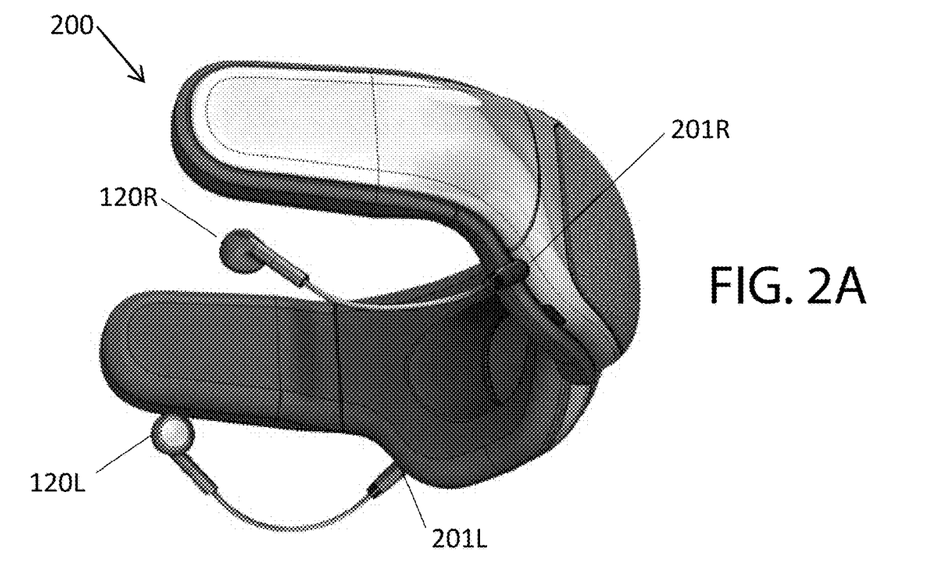
Figures 2B, 2C:
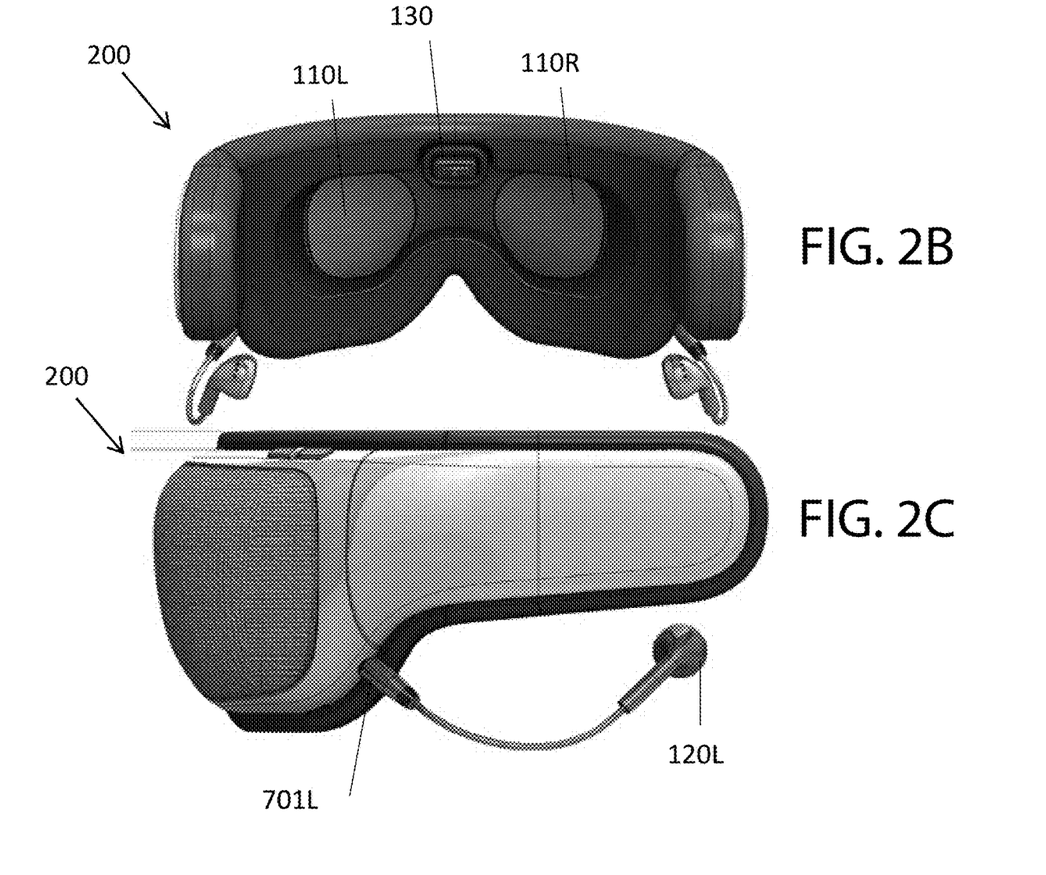
Figure 3:
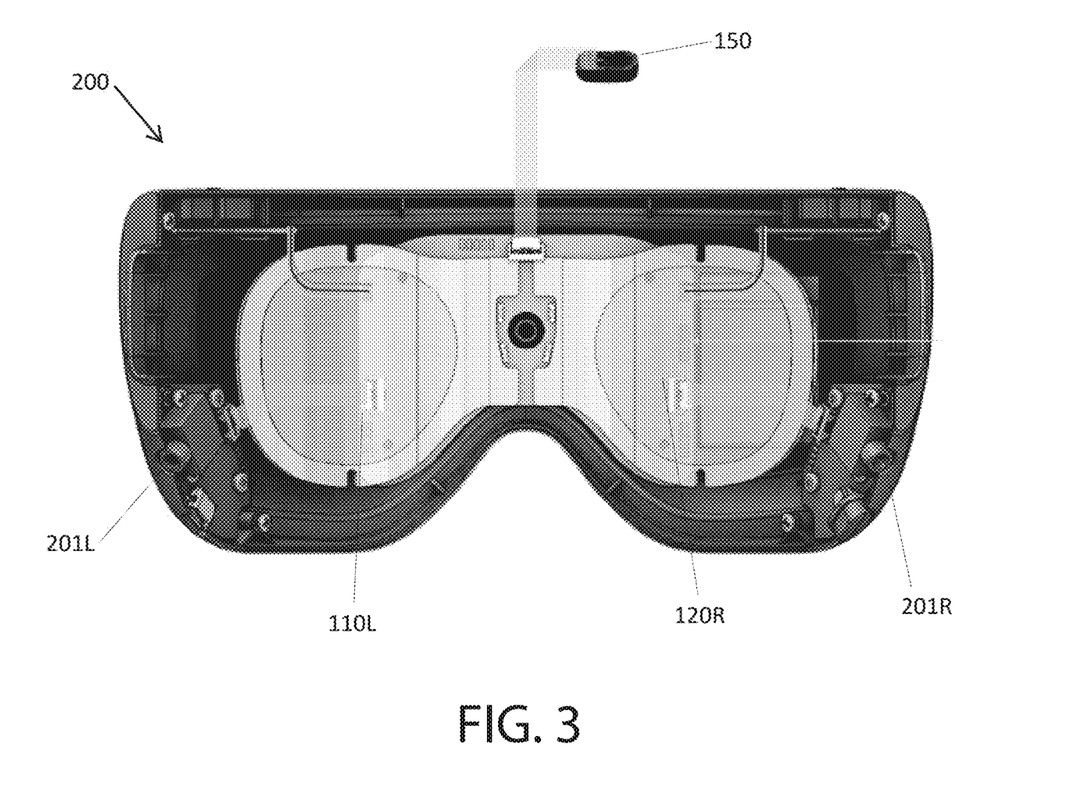
FIG. 3 is an exploded front view of one embodiment of a headset according to the system of FIG. 1.

FIGS. 2A, 2B, and 2C are a bottom right perspective view, a rear view, and a left view, respectively, and FIG. 3 is an exploded front view headset 200, which is generally similar to system 100 except as explicitly noted.

Headset 100 includes sensor assembly 150, controller 130, light sources 110L and 110R, and vibration sources 120L and 120R. Sensor assembly 150 also includes a biometric sensor system, such as that which is sold under the name of VALENCELL BENCHMARK™ (Raleigh, N.C.), that includes an infrared light source and detector, which can be used to detect heart rate using pulse oximetry, an accelerator, and a processing unit. Sensor assembly 150 includes a sensor module circuit board that contains a digital optical detector system. This detector controls the LEDs and converts the optical signals reflected from the user's skin to digital format and communicates over the internal I2C bus to the PerformTek® processor. The accelerometer is also read via the internal I2C bus for activity signal.

In one embodiment, controller 130 includes a Nordic Semiconductor ASA (Oslo, Norway) model NRF51822 Multiprotocol BLUETOOTH® low energy/2.4 GHz RF System on Chip, and a VLSI Solution (Tampere, Finland) model VS1000 audio module.

In one embodiment, light sources 110L and 110R are Lite-On, Inc. (Milpitas, Calif.) Bin G3/W2/AU model LTST-020VSKT LEDS. In one embodiment, vibration sources 120L and 120R are Basen Technology Co, Ltd model PN: OEM-E170a earbuds.

In one embodiment, sensor assembly 150 also includes a PerformTek® processor which polls sensor data over the internal I2C bus and converts the raw measurements into data registers of biometric values (i.e. Heart Rate, Cadence, VO2) and processes those values further into higher level user assessments (i.e. Calories Burned, Distance, VO2 max, fitness level, and the period between heart rate beats (the Heart Rate Interval, or RR Interval)). The PerformTek® processor runs algorithms to convert the raw signals to a register array of biometric values and high-level assessments. These values are available for reading via the UART or I2C firmware interface. In addition, sensor module diagnostics such as signal quality, error codes, and serial number ID are available.

Sensor assembly 150 further includes control lines for interfacing controller 130 with the PerformTek® processor include a Power On Self-Test (POST), UART or I2C communication interface, and a wake-from-standby line (WAKE). The host processor can control much of the functionality of the sensor module via a software protocol interface over the UART or I2C interface.

In one embodiment, sensor assembly 150 determines a current heart rate, and/or an inter-beat R-R interval which is provided to controller 130. In another embodiment, sensor assembly 150 also provides accelerometer data to controller 130.

In yet another embodiment, sensor assembly 150 includes one or more EEG sensors, as are known in the field, and provides brain electrical activity measurements to controller 130.

In another embodiment, sensor assembly 150 includes one or more EMG sensors positioned, for example and without limitation, to measure eye movement to ascertain when REM sleep is reached, and/or to measure muscle tone to aid in determining states of relaxation. EMG sensors, as are known in the field, and provides brain electrical activity measurements to controller 130.

Headset 200 also includes left and right audio jacks 101L and 101R into which left and right earbuds 120L and 120R, respectively, may be plugged into. Alternatively, stereo headphones (not shown) may be plugged into one of jacks 101L or 101R, where the jacks are appropriately programmed to provide stereo sound to the headphones.

Figure 4:
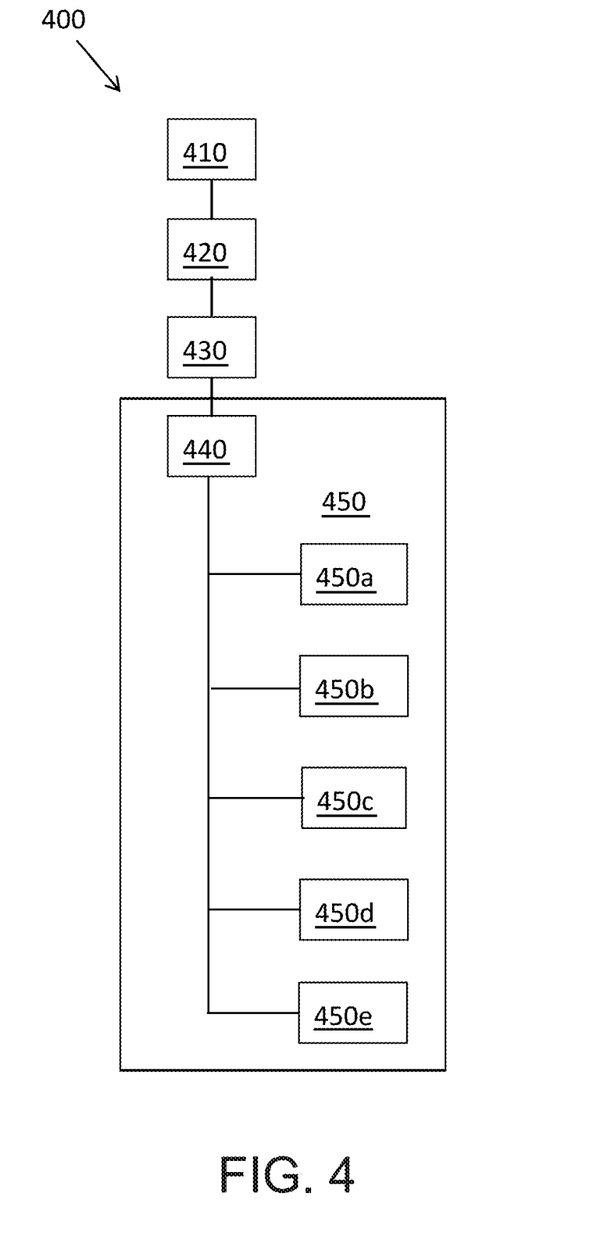
FIG. 4 is a flow chart of an exemplary method for providing therapeutic auditory, visual, and/or tactile stimulus.

FIG. 4 shows a flow chart of an exemplary method 400 for providing therapeutic auditory, visual, and/or tactile stimulus using, for example and without limitation, one of system 100 or headset 200. In a step 410, a subject having pain, or who wishes to undergo a treatment for managing pain, is identified. In a step 420, the subject is provided the therapeutic system or headwear, such as headset 200 as described above, and in step 430, the subject places the headset on their head. In a step 440, headset 200 executes programming 450 provided in controller 130 to provide stimuli to the subject. The programming provides two or more of auditory, visual, and/or tactile stimulus to the subject, and thus, for example, may provide power to activate left light source 110L, right light source 110R, left vibration source 120L and or right vibration source 120R. The programming also includes modifying the auditory, visual, and/or stimuli in response to measurements obtained by sensor assembly 150 and provided to controller 130.

As discussed above and herein, the left vibration source 120L and the right vibration source 120R may each comprise bone conduction transducer that may provide both auditory and tactile stimulus.

In certain embodiments, providing two or more of auditory, visual, and/or tactile stimulus concurrently may provide improved therapeutic benefits as compared to providing only one of auditory, visual, or tactile stimulus at one time. The two or more auditory, visual, and/or tactile stimulus may thus combine to provide the improved therapeutic benefits, for example (i.e., the two or more auditory, visual, and/or tactile stimulus may synergize in a way to provide improved results over providing two of the stimuli individually.)

Exemplary instructions for providing stimuli may be provided, for example, by programming 450, which includes one or more subroutines. One such subroutine is subroutine 450e, which analyzes measurements obtained from sensor assembly 150 and stores the analyzed measurements in memory 113. Subroutine 450a includes instructions for the simultaneous activation of all active auditory, visual, and/or tactile stimulus sources. Optionally, the activation of all sources may include the activation of tactile stimulation to run throughout all subsequent auditory and/or visual stimulation. Another exemplary subroutine 450b may include instructions for alternating the left auditory, visual, and/or tactile stimulus sources with the right auditory, visual, and/or tactile stimulus sources (i.e., the left stimuli and right stimuli take turns being active). Another exemplary subroutine 450c may include instructions for alternating the visual sources with the auditory and/or tactile sources (i.e., the visual stimuli and the auditory/tactile stimuli take turns being active). Another exemplary subroutine 450d may include instructions for alternating the left auditory and/or tactile source and the right visual source with the right auditory and/or tactile source and the left visual source (i.e., opposite auditory/tactile stimuli take turns being active).

In certain optional embodiments, one or more of subroutines 450a, 450b, 450c, or 450d, access the analyzed measurements from subroutine 450e and modifies the instructions they provide to the auditory, visual, and/or tactile stimuli depending on real-time or near real-time measurements of the user obtained from sensor assembly 150. Such programming is further described below.

In step 440, programming 450, including by not limited to subroutines 450a, 450b, 450c, and 450d, may each be applied one or more times, individually or in combination with one another. The programming may, in addition, provide sequences of output in subroutines 450a, 450b, 450c, and 450d at different frequencies and/or timings. Thus, for example the subroutines may provide output at specific frequencies that change as the subroutine is repeated.

In certain embodiments, the pulses that determine the amplitude modulation above are essentially square waves and thus, as determined by a Fourier analysis, are formed of sinusoidal components at the pulse frequency and at higher harmonics. As an approximation, an ideal square wave with a pulse frequency of P contains only odd-integer harmonic frequencies at $(2k-1)*P$, where $k=1, 2, 3 \ldots$, which contain a fraction $(2/\pi)/(2k-1)$ of the total power in the square wave. Thus, for example, the signal power in a square wave with a pulse frequency of 4 Hz includes a 63% of the power at 4 Hz, 21% of the power at 12 Hz, 13% of the power at 20, etc., If the square wave does not have equal on and off periods, then the pulse frequency will also contain even-integer harmonic frequencies.

Thus, for example, subroutine 450a may provide amplitude modulated auditory output to vibration source 120R or 120L at a carrier audio frequency of 256 Hz that is turned on and off, that is it is pulsed, at a pulse frequency of 1 Hz for 2 minutes, or may provide amplitude modulated light output to light source 110R or 110L that produces at a carrier light wavelength 580 nm that is turned on and off, that is it is pulsed at a at a pulse frequency of 1 Hz for 2 minutes. This square pulse auditory or light signal thus generates signals at a frequency of 1 Hz in addition to higher harmonics.

In certain embodiments, the subroutines described herein generate pulses having sinusoidal components that correspond with certain known brain wave frequencies, which are generally accepted as being delta waves (0.1 to 4.0 Hz), theta brain waves (4 to 7 Hz), alpha brain waves (8 to 15 Hz), beta waves (16 to 31 Hz), and gamma brain waves (32 to 100 Hz). Thus, certain embodiments include pulse frequencies of from 3.75 Hz to 4.25 Hz (theta brain waves), of from 1.25 Hz to 1.75 Hz (delta waves), and/or from 0.25 Hz and 0.75 Hz (delta waves).

In addition, by alerting the output between left and right channels, the brain may be stimulated in a way that it is forced to communicate between the left and right sides of the brain. This forced communication, for example, can allow PTSD memories to be wired to both sides of the brain, thereby stopping undesirable flashbacks. It can also create an enhanced relaxation effect, allowing for deeper relaxation and pain management.

In one embodiment, system 100 provides a stimulus that includes visual and auditory stimuli over three temporally sequential segments—a first segment where stimuli occurs at a first frequency, followed by a second segment where stimuli occurs at a second frequency, which was followed by a third segment where stimuli occurs at a third frequency. Each time segment included sub-segments of visual and auditory stimuli, where each sub-segment was determined by one of the subroutines described above, for example. The visual stimuli were provided by pulsing light at a wavelength of 580 nm at certain pulse frequencies and by pulsing auditory signals at a frequency of 256 Hz at certain pulse frequencies.

Figure 5:
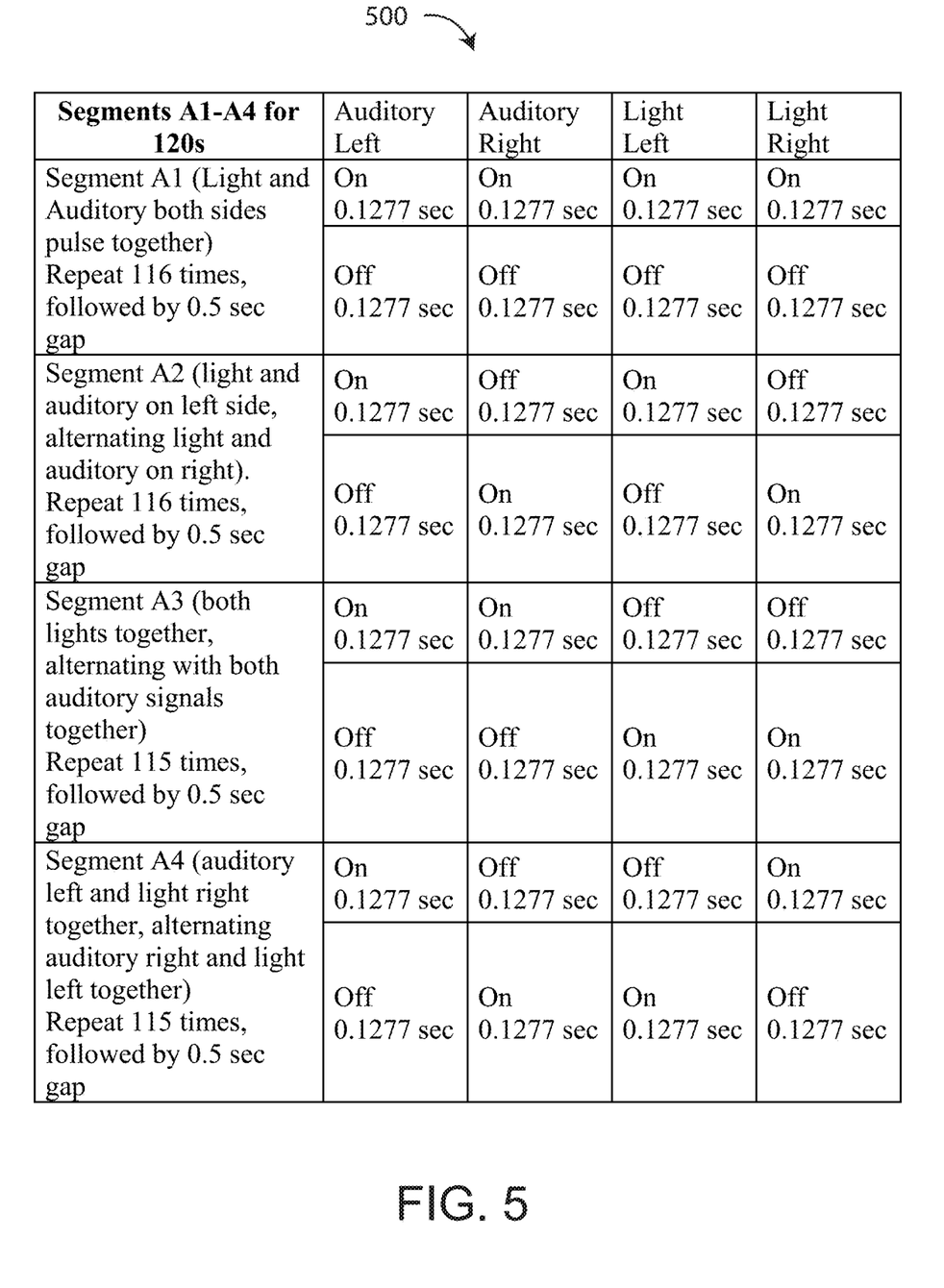
FIGS. 5, 6, and 7 are tables illustrating several treatment stimulus segments of FIG. 4.
Figure 6:
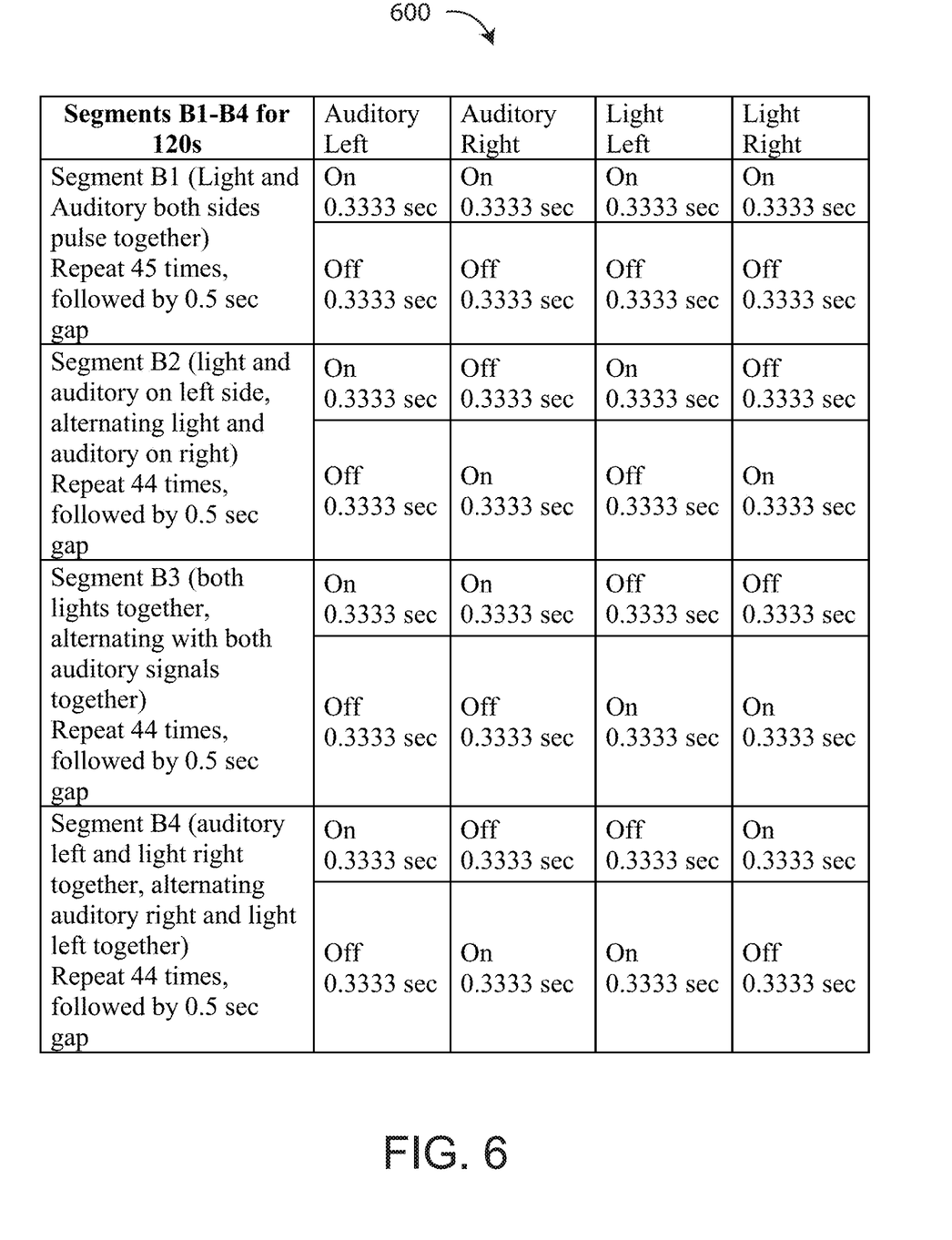
Figure 7:
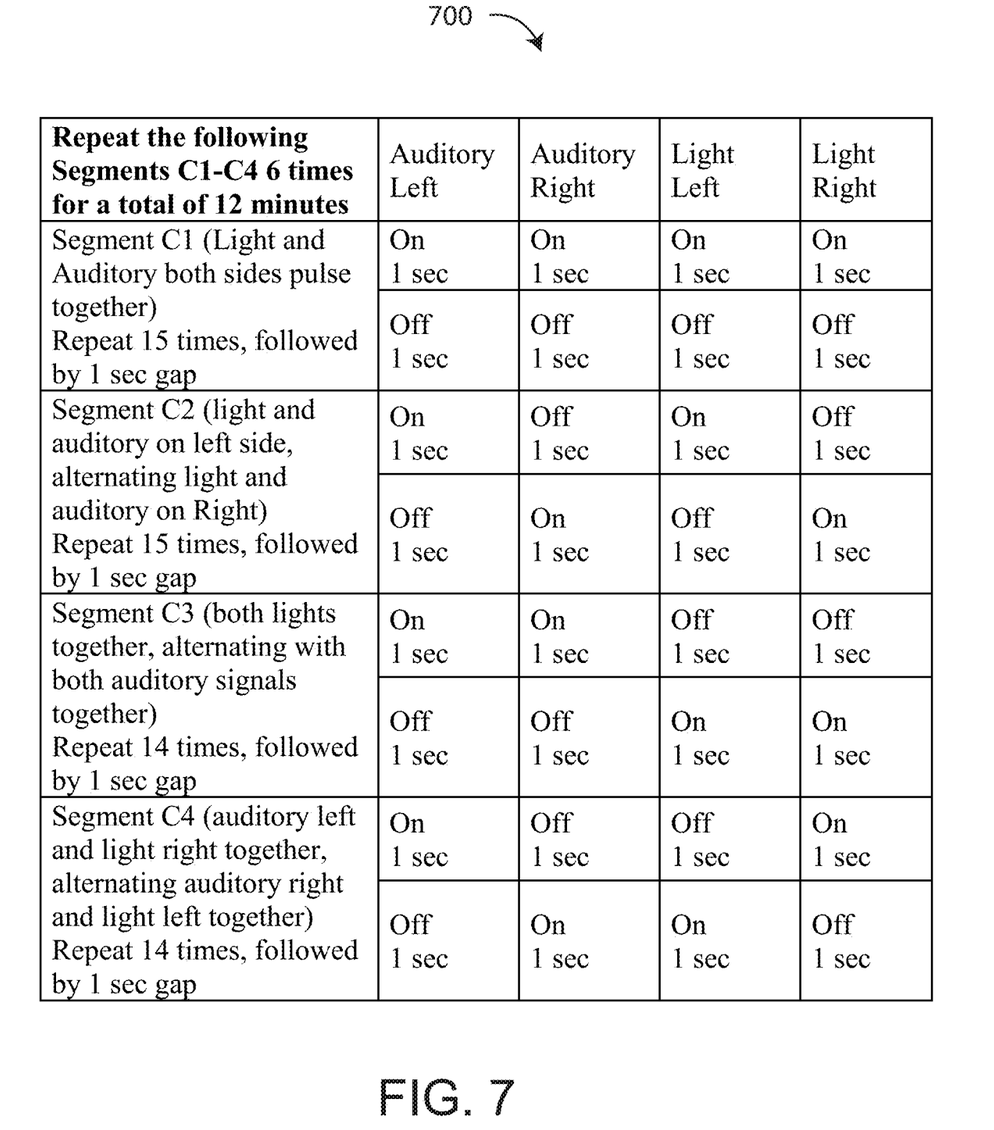

In one embodiment, a treatment stimulus lasted for 16 minutes, and may be understood by reference to Table 500 in FIG. 5, Table 600 in FIG. 6, and Table 700 in FIG. 7, where Table 500 contains specifications for the first segment ("Segment A"), Table 600 contains specifications for the next, second time segment ("Segment B"), and Table 700 contains specifications for the last time segment ("Segment C"). Each of the Segments stimuli patterns at a different pulse frequency. Specifically, Segment A cycles the stimuli through a block of four Segment A stimuli patterns for a total of 2 minutes, Segment B cycles the stimuli through a block of four Segment B stimuli patterns for a total of 2 minutes, and Segment C cycles the stimuli through a block of six Segment C stimuli patterns for a total of 12 minutes.

More specifically, in the four Segment A stimuli patterns, as shown in Table 500 as Blocks A1, A2, A3, and A4 respectively, the auditory and light outputs cycle 115 or 116 times between being on for 0.1277 seconds and then being off for 0.1277 seconds (that is, at a pulse frequency of 3.9 Hz), followed by no output for 0.5 seconds. In the Segment B stimuli patterns, as shown in Table 600 as Blocks B1, B2, B3 and B4, the auditory and light outputs cycle 44 or 45 times between being on for 0.3333 seconds and then being off for 0.3333 seconds (that is, at a pulse frequency of 1.5 Hz) followed by no output for 0.5 seconds. In the Segment C stimuli patterns, as shown in Table 700 and labeled Blocks C1, C2, C3 and C4, the auditory and light outputs cycle 14 or 15 times between being on for 1 second and then being off for 1 second (that is, a pulse frequency of 0.5 Hz), followed by no output for 1 second. Blocks A1, B1, and C1 pulse the right and left sides of both the light and auditory together, with all outputs are synchronized to be on or off at the same time, as provided by subroutine 450a. Blocks A2, B2, and C2 synchronize the left side light and auditory output, and the right side light and auditory output to be opposite to one another, as provided by subroutine 450b. Blocks A3, B3, and C3 synchronize both lights together to be opposite to both auditory outputs, as provided by subroutine 450c. Blocks A4, B4, and C4 synchronize the right auditory and light to be opposite to the left auditory and light outputs, as provided by subroutine 450d.

In step 440, subroutine 450e receives measurements from sensor assembly 150 and stores analyzed measurements. In one embodiment, sensor assembly 150 provides instantaneous, or nearly instantaneous, measurements from the user. Thus, for example and without limitation, sensor assembly 150 provides a sequence of measurements of beat-to-beat intervals of the heart of the user, that is, the time interval between the last two heart beats, which is also referred to, without limitation, as the RR intervals. Controller 130 then computes and stores values of the heart rate variability (HRV), which is a mathematical representation of the physiological phenomenon of variation in the time interval between heartbeats.

In certain embodiments, a time-domain calculation of RR intervals, as obtained by sensor assembly 150, is used to compute the HRV. Thus, for example, the sequence of RR intervals ("$RR_i$") is accepted from sensor assembly 150 and stored in memory 133. After the accumulation $RR_i$ for a period of time, T, the HRV is calculated as approximated by the root mean square of successive differences between adjacent RRs, or RMSSD. Thus, at a time T from the beginning of the accumulation of data, if N consecutive RR intervals are stored in memory 133, the following calculation is performed in processor 134 according to a program stored in the memory:

$$RMSSD = \sqrt{\frac{1}{N-1}\left(\sum_{i=1}^{N-1}(RR_{i+1} - RR_i)^2\right)}$$

The initial value of RMSSD (that is, $RMSSD_0$) is stored in memory 133 as a baseline. Thereafter, at the end of each period T, the calculation of RMSSD is repeated covering that time period. As a result, a sequence of $RMSSD_j$ values are computed. Next the difference between the current RMSSD value and the baseline $RMSSD_0$ is computed as $\Delta RMSSD_j = RMSSD_j - RMSSD_0$. $\Delta RMSSD$ is a measure of the change between the current HRV and the baseline, initial HRV.

In general, it is realized by those skilled in the art, that an increased in HRV is associated with a relaxed state, or a sleep state, and that a decrease in HRV is associated with a less relaxed, or stressed, state. For uses of therapeutic system 100 intended to calm a person or to induce sleep, a positive $\Delta RMSSD$ indicates that the person is becoming relaxed and that the system is working as intended. A negative $\Delta RMSSD$ indicates that the person is not becoming more relaxed. In one embodiment, an indication that the person is relaxed ($\Delta RMSSD > 0$) is used to modify the treatment by reducing the treatment time and/or intensity of the stimuli, and an indication that the person is less relaxed ($\Delta RMSSD < 0$) is used to modify the treatment to increase the treatment time and/or the intensity of the stimuli.

In certain embodiments, Kubios HRV software (manufactured by Kuopio, Finland) is used to analyze the RR intervals to provide additional HRV related data. Thus, for example, one useful measure for analyzing HRV is the fraction of the power of the HRV signal that occurs in certain frequency ranges. Thus, for example, one measure which is referred to herein as HRV-HFnu is obtained by taking the Fourier transform of the HRV signal and computing the ratio of the power of the HRV signal from 0.15 to 0.40 Hz ("high frequencies") to the total power of the HRV signal The calculations described above are provided by way of explanation and are not meant to limit the scope of the calculations or how the operation of therapeutic system 100 is or is not modified using HRV measurements.

Although the above steps show method 400 of treating a patient in accordance with embodiments, a person of ordinary skill in the art will recognize many variations based on the teaching described herein. The steps may be completed in a different order. Steps may be added or deleted. Some of the steps may comprise sub-steps. Many of the steps may be repeated as often as beneficial to the treatment.

One or more of the steps of the method 400 may be performed with the circuitry as described herein, for example, circuitry of the controller 130 or the external control unit 130a such as one or more of a processor or logic circuitry such as a central processing unit (CPU) or a programmable array logic for field programmable gate array. The circuitry may be programmed to provide one or more of the steps of the method 400, and the program may comprise program instructions stored on a computer readable memory or programmed steps of the logic circuitry such as the programmable array logic or the field programmable gate array, for example.

Measures of Withdrawal Symptoms

In the study discussed subsequently, test subjects were provided with a number of sensory stimuli and their response to the treatment was determined using subjective measures of the effect of withdrawal using questionnaires, mostly in the form of Visual Analog Scale ("VAS") surveys, that the person completed before, during, and after treatment. The measures included the following:

Subjective Opiate Withdrawal Scale ("SOWS"), in which subjects grade the intensity of 16 opioid withdrawal symptoms on a scale of 0 (not at all) to 4 (extremely). The symptoms measured using SOWS includes, the occurrence of: anxiety, sleepiness, sweating, tearing of the eyes, running of the nose, goosebumps, shaking, hot flushes, cold flushes, bones and muscles aching, restlessness, nausea, vomiting, muscle twitching, stomach cramps, and feeling the need of using an opioid. See, for example, https://www.ncbi.nlm.nih.gov/books/NBK143183/bin/annex10-fm2.pdf;

Desire to Use/Need to Use VAS, or VAS-Desire, in which subjects grade the intensity of cravings. See, for example. See, for example, Kozlowski, L. T., Mann, R. E., Wilkinson, D. A., & Poulos, C. X. (1989). "Cravings" are ambiguous: Ask about urges or desires. Addictive Behaviors, 14(4), 443-445;

VAS-Anxiety, in which subjects rate their perceived level of anxiety as being between "Not at all anxious," which is assigned a value of zero, and "Very anxious," which is assigned a value of 10. See, for example, Davey, H. M., Barratt, A. L., Butow, P. N., & Deeks, J. J. (2007). A one-item question with a Likert or Visual Analog Scale adequately measured current anxiety. Journal of clinical epidemiology, 60(4), 356-360; and VAS-Pain, in which subjects rate their perceived level of pain as being between "No Pain," which is assigned a value of zero, and "Worst Pain Imaginable," which is assigned a value of 10.

Patient-Reported Outcomes Measurement Information System of Sleep Disturbance (PROMIS-Disturbance) is an initiative from the National Institutes of Health to standardize the measurement of common physical and mental diseases, disorders, and conditions. The Sleep Disturbance Scale comprises four separate sub-scales: Quality, Refreshing, Problems, and Difficulty Falling Asleep. The items are then added together, and the resulting estimate can be converted to a standardized measure. Higher scores indicate greater levels of sleep disturbance.

EXAMPLES

Antidotal Evidence

Headset 200 has been used in a number of studies, for example, to examine the effects on the headset for improving sleep and in relieving pain. During these studies, the inventor discovered that subjects reported that the use of headset 200 lessened the effects of withdrawal from nicotine addiction.

Pilot Study

A study was conducted on the effectiveness of the inventive method for treating symptoms of opioid addiction withdrawal using a double-blind, randomized, controlled cross-over study of 8 subjects (for a total of 16 subject experiences). The subjects were patients of an inpatient treatment program in which they were receiving daily doses of 60-80 mg of methadone. The demographics of the subjects largely mirroring a methadone-maintained population. There was no attrition and all assessments, as described below, were completed as planned per protocol. The protocol provides for the use of device (headset 200) at regularly scheduled intervals, as described below.

In this study, the effectiveness of headset 200 was tested by having each subject undergo two separate treatment regimes. One regime is referred to herein as an "Active Treatment," in which subjects were provided with sound and light according to the sequences described above. The other regime is referred to herein as a "Sham Treatment," in which subjects were provided with light and sound using headset 200 which was programmed to provide light and sound at levels that were not therapeutic in nature. Specifically, for the Sham Treatment, headset 200 was programmed to deliver a 232 Hz tone for a short period at the start of 5-minute cycles of the light turning on, then off, then on.

The pilot study proceeded as follows. On a first day, each patient received their normal dose of methadone and was provided with a headset 200, along with instructions on its use. The programming of headset 200 was randomly selected to provide the subject with either an Active Treatment or a Sham Treatment, as described above. Baseline scores were collected within 12 hours of taking their methadone, including SOWS, Desire to Use/Need to Use VAS, Anxiety VAS, and Pain VAS scores, and for PROMIS-Disturbance for the night before the first day. During the first day, the subjects used the appropriately programmed headset 200 (either as an Active Treatment or a Sham Treatment) to receive three treatments, at approximately 16:00, 20:00, and 22:00 to 24:00 (prior to bedtime).

On the following, second day, referred to herein as the "treatment day," subjects were not allowed to take their normal dose of methadone. The subjects used the appropriately programmed headset 200 to receive five Active Treatments or Sham Treatments over an approximately 16-hour awake period, starting at approximately 8:00 am, with the last treatment prior to bedtime (e.g., at approximately 08:00, 12:00, 16:00, 20:00, and 22:00 to 24:00).

During the treatment day, scores from each subject was obtained using the SOWS, Desire to Use/Need to Use VAS, VAS-Anxiety, and VAS-Pain on the following schedule: 1) prior to the first morning treatment session; 2) within 5 minutes after each treatment; and 3) 2 hours after the end of the first 4 planned treatments. PROMIS-Disturbance scores were obtained for the night of the treatment day.

On the morning of day following treatment day, follow-up scores from each subject was obtained using the SOWS, Desire to Use/Need to Use VAS, Anxiety VAS, and Pain VAS and the subjects were permitted to resume their normal methadone treatment. PROMIS-Disturbance scores were obtained for the night of the treatment day. Subjects then continued their normal methadone treatment for at least 7 days to allow for a return to steady-state methadone levels between treatments. Each subject was then provided with the other treatment on the same schedule as described above.

There were three occasions during the study where subjects needed a dose of rescue medication. For those subjects, there were no measures taken after exposure for the remainder of the treatment day. The use of the Active Treatment resulted in less frequent use of rescue medications as compared to the Sham Treatment.

Table 1 presents the SOWS scores averaged by treatment condition. A SOWS score of 0-10 is mild withdrawal, 11-20 is moderate, and 21+ is severe. The columns of data in Table 1 are: Baseline mean, presenting SOWS score by condition; Treatment, presenting SOWS score on treatment day per subject, then averaging by condition; Treatment(Max), presenting the largest SOWS score on treatment day per subject, then averaging by condition; and Follow-Up, presenting the mean SOWS score on the day following treatment day per subject, then averaging by condition.

TABLE 1

SOWS by Treatment Condition.

|  | Baseline | Treatment | Treatment(Max) | Follow-up |
|---|---|---|---|---|
| Active Treatment | 0.5 | 4.0 | 9.2 | 13.9 |
| Sham treatment | 1.0 | 5.8 | 12.0 | 9.5 |

The results in Table 1 indicate that the Active Treatment resulted in a lower average and maximum SOWS scores than the Sham Treatment on the treatment day. Thus, headset 200 provided a therapeutically effective amount of a sensory stimulus for treating, during opioid withdrawal, the combination of anxiety, sleepiness, sweating, tearing of the eyes, running of the nose, goosebumps, shaking, hot flushes, cold flushes, bones and muscles aching, restlessness, nausea, vomiting, muscle twitching, stomach cramps, and feeling the need of using an opioid.

Table 2 presents the VAS-Anxiety score by treatment condition, where the VAS-Anxiety score is used to rate the intensity of anxiety with higher numbers indicate more adverse outcomes. The columns of data in Table 2 are: Baseline mean, presenting VAS-Anxiety score by condition; Treatment, presenting VAS-Anxiety score on treatment day per subject, then averaging by condition; Treatment(Max), presenting the largest VAS-Anxiety score on treatment day per subject, then averaging by condition; and Follow-Up, presenting the mean VAS-Anxiety score on the day following treatment day per subject, then averaging by condition.

TABLE 2

VAS-Anxiety by Treatment Condition.

|  | Baseline | Treatment | Treatment(Max) | Follow-up |
|---|---|---|---|---|
| Active Treatment | 6.7 | 11.2 | 18.1 | 24.2 |
| Sham Treatment | 8.7 | 17.9 | 29.0 | 23.5 |

The results in Table 2 indicate that the Active Treatment resulted in a lower average and maximum VAS-Anxiety scores than the Sham Treatment on the treatment day. Thus, headset 200 provided a therapeutically effective amount of a sensory stimulus for treating anxiety during opioid withdrawal.

Table 3 presents the VAS-Need to Use Opioid (or "VAS-N") scores averaged by treatment condition. Lower scores indicate less need to use, whereas higher scores at the high end indicate a greater need to use. The columns of data in Table 3 are: Baseline mean, presenting VAS-N score by condition; Treatment, presenting VAS-N score on treatment day per subject, then averaging by condition; Treatment (Max), presenting the largest VAS-N score on treatment day per subject, then averaging by condition; and Follow-Up, presenting the mean VAS-N score on the day following treatment day per subject, then averaging by condition.

TABLE 3

VAS-N by Treatment Condition.

|  | Baseline | Treatment | Treatment(Max) | Follow-up |
|---|---|---|---|---|
| Active Treatment | 4.6 | 12.7 | 23.6 | 27.6 |
| Sham Treatment | 3.4 | 21.6 | 32.7 | 25.5 |

The results in Table 3 indicate that the Active Treatment resulted in a lower average and maximum VAS-N scores than the Sham Treatment on the treatment day. Thus, headset 200 provided a therapeutically effective amount of a sensory stimulus for decreasing the need to use an opioid during opioid withdrawal.

Table 4 presents the VAS-Desire to Use Opioid (or "VAS-D") scores averaged by treatment condition. Lower scores indicate less desire to use, whereas higher scores at the high end indicate a greater desire to use. VAS-D is conceptually related to the VAS-N, except that it captures the cognitive aspect of addiction compared to the VAS-N, which captures the physical/mental compulsion to use. The columns of data in Table 4 are: Baseline mean, presenting VAS-D score by condition; Treatment, presenting VAS-D score on treatment day per subject, then averaging by condition; Treatment(Max), presenting the largest VAS-D score on treatment day per subject, then averaging by condition; and Follow-Up, presenting the mean VAS-D score on the day following treatment day per subject, then averaging by condition.

TABLE 4

VAS-D scores by Treatment Condition.

|  | Baseline | Treatment | Treatment(Max) | Follow-up |
|---|---|---|---|---|
| Active Treatment | 14.0 | 13.2 | 2.8 | 20.8 |
| Sham Treatment | 18.0 | 21.3 | 9.5 | 21.0 |

The results in Table 4 indicate that the Active Treatment resulted in a lower average and maximum VAS-D scores than the Sham Treatment on the treatment day. Thus, headset 200 provided a therapeutically effective amount of a sensory stimulus for decreasing the desire to use an opioid during opioid withdrawal.

Table 5 presents the VAS-Pain scores averaged by treatment condition. Lower scores indicate less desire to use, whereas higher scores at the high end indicate a greater desire to use. The columns of data in Table 5 are: Baseline mean, presenting VAS-Pain score by condition; Treatment, presenting VAS-Pain score on treatment day per subject, then averaging by condition; Treatment(Max), presenting the largest VAS-Pain score on treatment day per subject, then averaging by condition; and Follow-Up, presenting the mean VAS-Pain score on the day following treatment day per subject, then averaging by condition.

TABLE 5

VAS-Pain scores by Treatment Condition.

|  | Baseline | Treatment | Treatment(Max) | Follow-up |
|---|---|---|---|---|
| Active Treatment | 12.3 | 18.0 | 25.8 | 26.6 |
| Sham Treatment | 20.3 | 20.0 | 26.5 | 23.6 |

The results in Table 5 indicate that the Active Treatment resulted in a lower average and maximum VAS-Pain scores than the Sham Treatment on the treatment day. Thus, headset 200 provided a therapeutically effective amount of a sensory stimulus for decreasing pain during opioid withdrawal.

Table 6 presents the PROMIS Sleep Scale Problems (Disturbance) scores averaged by treatment condition. Higher scores indicate greater levels of sleep disturbance. The columns of data in Table 5 are: Baseline mean, presenting Disturbance score by condition; Treatment, presenting Disturbance score on the evening of treatment day per subject, then averaging by condition; and Follow-Up, presenting the mean Disturbance score on the day following treatment day per subject, then averaging by condition.

TABLE 6

PROMIS Sleep Scale Problems (Disturbance) scores by Treatment Condition.

|  | Baseline | Treatment | Follow-up |
|---|---|---|---|
| Active Treatment | 9.6 | 8.0 | 10.3 |
| Sham Treatment | 9.4 | 10.0 | 13.6 |

The results in Table 6 indicate that the Active Treatment resulted in a lower average Disturbance score than the Sham Treatment following the treatment day. Thus, headset 200 provided a therapeutically effective amount of a sensory stimulus for improving sleep during opioid withdrawal.

In summary, the results of the pilot study of the use of headset 200 to treat symptom of opioid withdrawal are: 1) subjects experienced less frequent use of rescue medications when undergoing Active Treatment compared to the Sham Treatment; and 2) SOWS, Desire to Use/Need to Use VAS, Anxiety VAS, Pain VAS and PROMIS-Disturbance scores for Active Treatment all showed improved outcomes relative to Sham Treatments.

One embodiment of each of the methods described herein is in the form of a computer program that executes on a processing system, e.g., a one or more processors that are part of a system 100. Thus, as will be appreciated by those skilled in the art, embodiments of the present invention may be embodied as a method, an apparatus such as a special purpose apparatus, an apparatus such as a data processing system, or a carrier medium, e.g., a computer program product. The carrier medium carries one or more computer readable code segments for controlling a processing system to implement a method. Accordingly, aspects of the present invention may take the form of a method, an entirely hardware embodiment, an entirely software embodiment or an embodiment combining software and hardware aspects. Furthermore, the present invention may take the form of carrier medium (e.g., a computer program product on a computer-readable storage medium) carrying computer-readable program code segments embodied in the medium. Any suitable computer readable medium may be used including a magnetic storage device such as a diskette or a hard disk, or an optical storage device such as a CD-ROM.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment. Furthermore, the particular features, structures or characteristics may be combined in any suitable manner, as would be apparent to one of ordinary skill in the art from this disclosure, in one or more embodiments.

Similarly, it should be appreciated that in the above description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

What is claimed is:
1. A method comprising:
   selecting a person undergoing an addiction withdrawal and having one or more withdrawal symptoms; and
   treating the one or more withdrawal symptoms by administering a therapeutically effective amount of a sensory stimulus to the person;

where said sensory stimulus comprises:
one or more visual stimuli; and
one or more auditory stimuli.

2. The method of claim 1, where said one or more withdrawal symptoms are chosen from sleepiness, sweating, tearing of eyes, running of a nose, goosebumps, shaking, hot flushes, cold flushes, aching bones, aching muscles, restlessness, nausea, vomiting, muscle twitching, stomach cramps, pain, a need to use an opioid, a desire to use an opioid, and sleep disturbances.

3. The method of claim 1, where the withdrawal symptoms result from opioid withdrawal.

4. The method of claim 1, where the withdrawal symptoms result from nicotine withdrawal.

5. The method of claim 1, where said method further reduces the person's use of rescue medications.

6. The method of claim 1, where said one or more visual stimuli include an amplitude modulated light source.

7. The method of claim 1, where one of said one or more visual stimuli includes a sinusoidally varying light source.

8. The method of claim 1, where one of said one or more auditory stimuli includes an amplitude modulated audio frequency.

9. The method of claim 1, where said sensory stimulus includes two or more sensory stimuli patterns including a first stimuli pattern that is different than a second stimuli pattern.

10. The method of claim 9, where said first stimuli pattern has a first pulse frequency and said second stimuli pattern has a second pulse frequency.

11. The method of claim 10, where said first stimuli pattern includes a first sinusoidal component that is between 3.75 Hz and 4.25 Hz, is between 1.25 Hz and 1.75 Hz, or is between 0.25 Hz and 0.75 Hz, and where said second stimuli pattern includes a second sinusoidal component that is between 3.75 Hz and 4.25 Hz, is between 1.25 Hz and 1.75 Hz, or is between 0.25 Hz and 0.75 Hz.

12. The method of claim 10, where said two or more sensory stimuli patterns includes a third stimuli pattern that is different than said first stimuli pattern and said second stimuli pattern.

13. The method of claim 12, where said first stimuli pattern includes a first sinusoidal component that is between 3.75 Hz and 4.25 Hz, is between 1.25 Hz and 1.75 Hz, or is between 0.25 Hz and 0.75 Hz, where said second stimuli pattern includes a second sinusoidal component that is between 3.75 Hz and 4.25 Hz, is between 1.25 Hz and 1.75 Hz, or is between 0.25 Hz and 0.75 Hz, and where said third stimuli pattern includes a third sinusoidal component that is between 3.75 Hz and 4.25 Hz, is between 1.25 Hz and 1.75 Hz, or is between 0.25 Hz and 0.75 Hz.

14. The method of claim 1, where said sensory stimulus alternates between
a first sensory stimuli including simultaneously providing a left visual stimuli pattern to a left eye of the person and a right auditory stimuli pattern to the right side of a head of the person, and
a second sensory stimuli including simultaneously providing a right visual stimuli pattern to a right eye of the person and a left auditory stimuli pattern to the left side of the head of the person,
wherein one or more of the left auditory stimuli pattern or the right auditory stimuli pattern comprises a sequence of stimuli patterns including a first stimuli pattern, a second stimuli pattern, and a third stimuli pattern.

15. The method of claim 14, further comprising:
periodically providing a sensory stimuli including simultaneously providing a left visual stimuli pattern to the left eye, a right visual stimuli pattern to the right eye, a left auditory stimuli pattern to the left side of the head, and a right auditory stimuli pattern to the right side of the head.

16. The method of claim 14, further comprising:
alternating sensory stimuli between
a third sensory stimuli including simultaneously providing a left visual stimuli pattern to the left eye and a left auditory stimuli pattern to the left side of the head, and
a fourth sensory stimuli including simultaneously providing a right visual stimuli pattern to the right eye and a right auditory stimuli pattern to the right side of the head.

17. The method of claim 16, further comprising:
alternating sensory stimuli between
a fifth sensory stimuli including simultaneously providing a left auditory stimuli pattern to the left side of the head and a right auditory stimuli pattern to the right side of the head, and
a sixth sensory stimuli including simultaneously providing a left visual stimuli pattern to the left eye and a right visual stimuli pattern to the right eye.

18. The method of claim 14, wherein the left auditory stimuli pattern comprises generating the left auditory stimuli pattern with a left speaker, and wherein generating the right auditory stimuli pattern comprises generating the right auditory stimuli pattern with a right speaker.

19. The method of claim 14, wherein the left auditory stimuli pattern comprises generating the left auditory stimuli pattern with a left bone conduction transducer of a headset, and wherein the right auditory stimuli pattern comprises generating the right auditory stimuli pattern with a right bone conduction transducer of the headset.

20. The method of claim 14, wherein one or more of the left or right auditory stimuli pattern includes an auditory frequency of from 240 Hz to 480 Hz.

21. The method of claim 14, wherein one or more of the left visual stimuli pattern or right visual stimuli pattern comprises repeatedly pulsing a light at one or more of a first pulse frequency, a second pulse frequency less than the first pulse frequency, or a third pulse frequency less than the first and second pulse frequencies.

22. The method of claim 21, wherein the first pulse frequency is between 3.75 Hz and 4.25 Hz, the second pulse frequency is between 1.25 Hz and 1.75 Hz, and the third pulse frequency is between 0.25 Hz and 0.75 Hz.

23. The method of claim 21, wherein repeatedly pulsing the light comprises pulsing the light for a predetermined time interval.

24. The method of claim 23, wherein the predetermined time interval is 25-45 seconds.

25. The method of claim 14, wherein the sequence of stimuli patterns each have a pulse frequency having a pulse period, where a portion of the pulse period includes a stimulus of an auditory frequency of from 240 Hz to 480 Hz.

26. The method of claim 25, wherein said portion of said pulse period is one half of the pulse period.

27. The method of claim 14, wherein said first stimuli pattern, said second stimuli pattern, or said third stimuli pattern stimulates for a predetermined time interval.

28. The method of claim 27, wherein the predetermined time interval is 25-35 seconds.

29. The method of claim 28, wherein the predetermined time interval is 30 seconds.

30. The method of claim 10, where said first stimuli pattern includes a first sinusoidal component corresponding to a first delta brain wave frequency, a first theta brain wave frequency, or a first alpha brain wave frequency, and where said second stimuli pattern includes a second sinusoidal component corresponding to a second delta brain wave frequency, a second theta brain wave frequency, or a second alpha brain wave frequency.

31. The method of claim 30, where said third stimuli pattern includes a third sinusoidal component corresponding to a third delta brain wave frequency, a third theta brain wave frequency, or a third alpha brain wave frequency, and where said second stimuli pattern includes a fourth sinusoidal component corresponding to a fourth delta brain wave frequency, a fourth theta brain wave frequency, or a fourth alpha brain wave frequency.

32. The method of claim 1, further comprising
obtaining at least one measurement of the person using at least one sensor;
determining a state of the person from the at least one obtained measurement; and
modifying said sensory stimulus according to said determined state of the person.

33. The method of claim 32, where said at least one sensor includes at least one heart rate sensor, at least one heart rate variability (HRV) sensor, at least one temperature sensor, at least one motion sensor, at least one galvanic skin response sensor, at least one accelerometer at least one EEG, at least one EMG.

34. The method of claim 33, where said determined state of the person is a state of sleep or a level or change in a level of relaxation or arousal.

35. The method of claim 1, further comprising:
providing a headset to be worn by the person; and
administering, with the headset, the therapeutically effective amount of a sensory stimulus to the person.

36. The method of claim 35, where the withdrawal symptoms result from opioid withdrawal.

37. The method of claim 35, where the withdrawal symptoms result from nicotine withdrawal.

* * * * *